US00PP36700P2

(12) United States Plant Patent
Hansen

(10) Patent No.: US PP36,700 P2
(45) Date of Patent: May 20, 2025

(54) ***HOSTA* PLANT NAMED 'Moment to Treasure'**

(50) Latin Name: ***Hosta* hybrid**
Varietal Denomination: Moment to Treasure

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,377

(22) Filed: Dec. 20, 2024

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./263.1, 353
See application file for complete search history.

(56) References Cited

U.S. PATENT DOCUMENTS

PP20,774 P2 * 2/2010 Skaggs ..... A01H 6/12 Plt./353
PP35,563 P2 * 12/2023 Hansen ..... A01H 6/12 Plt./353

* cited by examiner

*Primary Examiner* — Karen M Redden

(57) ABSTRACT

A new and distinct *Hosta* plant named 'Moment to Treasure' produces large rounded mounds of large, broadly ovate, variegated leaves with acute apices and cordate bases. The leaves are variegated having bluish-green margins, the centers the center is a golden yellow, with intermediate color separation between the margin and center of variably large segments of several shades of chartreuse. The large leaves are slightly bullate and glaucous on the top and bottom. The campanulate flowers are pale lavender appearing in late June and continuing for about three weeks. Each flower is attractively subtended by a floral bract that has a greenish margin with a pale yellow center and a chartreuse intermediate zone. 'Moment to Treasure' is useful in the landscape, as a container plant, a specimen, or en masse.

2 Drawing Sheets

Botanical classification: *Hosta* hybrid (Tratt.).
Variety denomination: 'Moment to Treasure'.

STATEMENT REGARDING PRIOR DISCLOSURES UNDER 37 CFR 1.77(B)(6)

*Hosta* 'Moment to Treasure' was first introduced by the inventor as a non-enabling description in registration of the name in early 2024 with the International Cultivar Registration Authority for the genus *Hosta*. No plants of *Hosta* 'Moment to Treasure' have been sold or offered for sale in this country or anywhere in the world, nor has any enabling disclosure of the new plant been made.

BACKGROUND AND ORIGIN OF THE PLANT

The present invention relates to a new and distinct *Hosta* plant named 'Moment to Treasure' hereinafter also referred to as the new plant or by the cultivar name, 'Moment to Treasure'. *Hosta* 'Moment to Treasure' was hybridized by the inventor on Jun. 25, 2015, at a wholesale perennial nursery in Zeeland, Michigan, USA. The female parent was a proprietary, unreleased, streaked sport of 'Elegans' known only as 14-SP-HOST-3001 (not patented) and the male parent was 'Viking Ship' not patented. A single seedling selection from this cross eventually was selected as the new plant. The new plant was assigned the breeder code 15-274-5 and passed the initial evaluation in the summer of 2018.

'Moment to Treasure' has been asexually propagated by division at the same nursery since 2022 and also by careful shoot tip plant tissue culture with the resultant asexually propagated plants having retained all the same traits as the original plant. The new plant is stable and reproduces true to type in successive generations of asexual reproduction. 'Moment to Treasure' has been stable and reproduced true-to-type plants in successive generations of asexual reproduction.

There are over 7,000 registered and established *Hosta* cultivars with The American *Hosta* Society, which is the International Cultivar Registration Authority for the genus *Hosta*. Several of these have green leaf blades with variegated margins. The most similar *Hosta* cultivars known to the applicant are: 'Avant Garde' Co-pending U.S. Plant patent application Ser. No. 18/831,373, 'Awakening Spirit' Co-pending U.S. Plant patent application Ser. No. 18/831,380, 'Great Expectations' (not patented), 'Brother Stefan' (not patented), 'Lean on Me' (not patented), 'Paradigm' (not patented), 'Seduced' (not patented), and 'Sound of Music' U.S. Plant Pat. No. 35,563.

The habit of 'Avant Garde' has slightly larger foliage that is less bullate, with a more acute apex, and the center color is more khaki. 'Great Expectations' has a slower growth rate, more erect taller scapes of near white flowers, thicker, stiffer, and more bullate foliage, and the leaf centers more creamy-colored and less yellowish. 'Paradigm' has a larger habit, the flower scapes are taller and more upright with lighter lavender flowers that open wider, and the foliage is larger, and more bullate. 'Brother Stefan' has a smaller habit with smaller narrower foliage, the scapes are taller with flowers of white. 'Lean on Me' has a larger habit, larger foliage, and taller flower scapes, and the leaf center is more chartreuse and not as yellowish. 'Seduced' has a smaller habit with smaller foliage having a lighter green margin and a slower growth rate. 'Sound of Music' has a larger habit and larger foliage and the scapes are more upright.

The female parent has a more bullate foliage that has a streaked variegation pattern with yellowish-chartreuse and bluish-green not confined to the margins or centers. The male parent has a larger more upright habit with larger more glaucous foliage, more rippled margins, lacks foliar variegation, and the flowers have more lavender coloration.

Other *Hosta* cultivars may have individual traits similar to 'Moment to Treasure' but the new plant differs from the above-listed cultivars and all other *Hostas* known to the applicant, by the combination of the following traits.

1. The habit is a large-sized rounded mound.
2. Leaves are variegated, large-sized, broadly ovate, with acute apices and cordate bases, slightly bullate, and slightly glaucous;
3. Leaf margins are bluish-green, the center color is golden yellow;
4. Numerous campanulate flowers of pale lavender on arching to outwardly scapes just above the foliage beginning in late June for about three weeks;
5. Floral bracts subtend each flower;
6. Bract color is greenish on the margin, pale yellow in the center with a chartreuse intermediate zone.

BRIEF DESCRIPTION OF THE DRAWING

The photograph of the new plant demonstrates the overall appearance of the new plant, including the unique traits. The colors are as accurate as reasonably possible with color reproductions. Ambient light spectrum, temperature, source, and direction may cause the appearance of minor variations in color.

The drawings show an eight-year-old 'Moment to Treasure' plant in a trial garden at a nursery in Zeeland, MI with supplement fertilizer and water as needed.

DETAILED BOTANICAL DESCRIPTION

Figure 1:
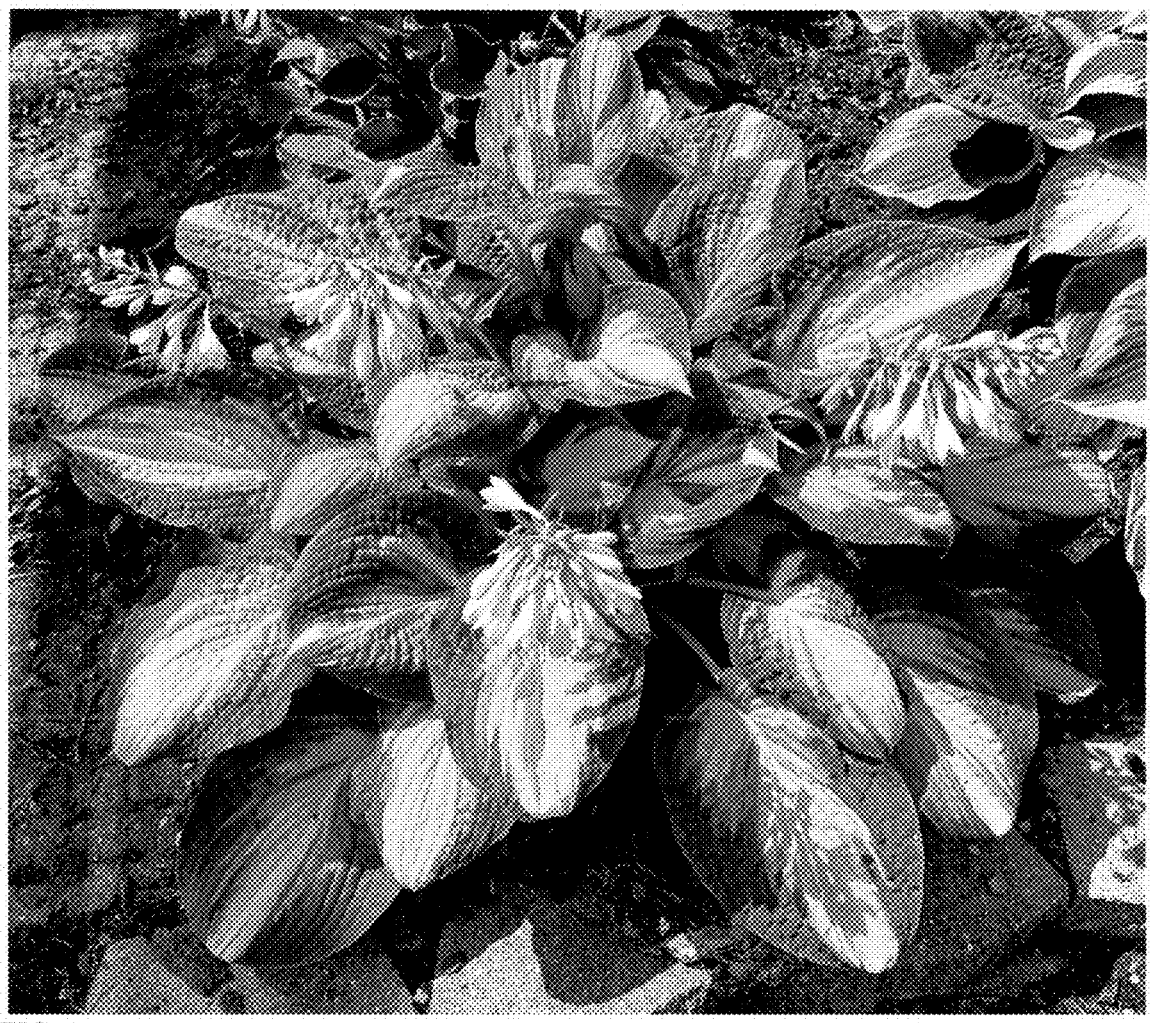
FIG. 1 shows the landscape foliage habit and color of the new plant.
Figure 2:
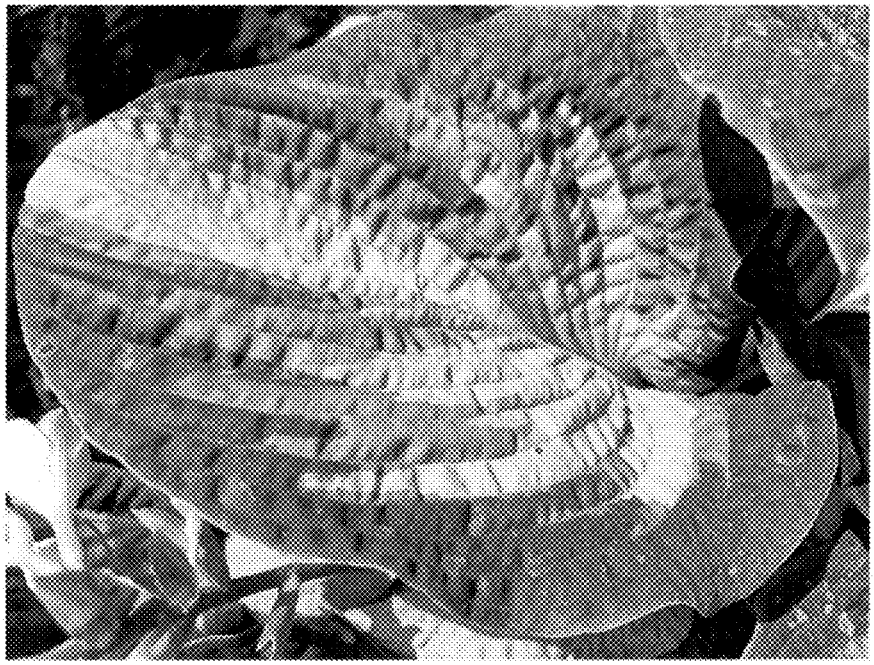
FIG. 2 shows a close-up of a leaf showing the variegation in summer.
Figure 3:
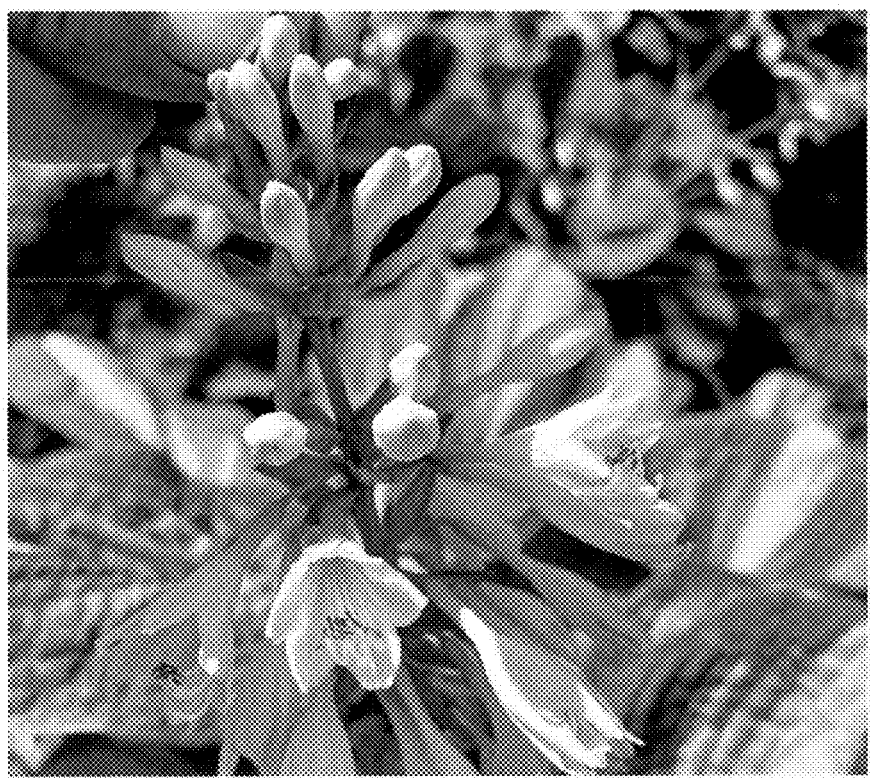
FIG. 3 shows a close-up of the scape with flowers, buds, and small floral bracts.

The following descriptions and color references are based on the 2015 edition of The Royal Horticultural Society Colour Chart except where common dictionary terms are used. The new plant, *Hosta* 'Moment to Treasure', has not been observed under all possible environments. Those skilled in the art would recognize the phenotype of the new plant would differ based on maturity level or number of years without dividing. The phenotype may vary slightly with different environmental conditions, such as temperature, light, fertility, moisture, and maturity levels, but without any change in the genotype. The following observations and size descriptions are of an eight-year-old plant in a shaded trial garden in Zeeland, Michigan with supplemental water and fertilizer.

Botanical classification: *Hosta* x hybrid;

Parentage: Female or seed parent is a proprietary sport of 'Elegans'; male or pollen parent is 'Viking Ship';

Propagation: Garden division and sterile shoot tip tissue culture;

Time to initiate roots from tissue culture: About three to four weeks;

Growth rate: Moderate;

Crop time: About five months to six months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with a basal rosette of leaves emerging from rhizomes producing a medium-sized mound of outwardly extending petioles and leaves and arching scapes flowering above the foliage;

Plant size: Foliage height to about 48 cm above the soil to the top of the leaves, to about 58 cm tall to the top of the flowers, and to about 109 cm wide at the widest point just above the soil line;

Foliage description: Broadly ovate; acute apex; cordate base; margin entire, and slightly sinuate; not folded, flat, and not bullate between the veins; glabrous and lightly glaucous on adaxial and abaxial; flexible; variegated;

Leaf blade size: To about 25.5 cm long and about 20.5 cm wide about one-third way from the base; average about 22.5 cm long and 18 cm wide;

Leaf blade color: Early season and expanding adaxial margin region nearest RHS 137A, center nearest RHS 146D, and intermediate zone between center and margin comprising between RHS N138D and RHS 137B, and nearest RHS 146B; early season and expanding abaxial margin region nearest RHS 137B, center nearest RHS 146D, with intermediate zone comprising RHS 146C, and 147B; mid-season and mature adaxial margin between RHS N138A and RHS NN137A, center between RHS 146D and RHS 145A, and intermediate zone comprising between RHS 144C and RHS N144D, RHS 138B, and between RHS 146B and RHS 147B; mid-season and mature abaxial margin between RHS 137B and RHS 189A, center between RHS 147C and RHS 146D, with intermediate zone comprising colors of nearest RHS 148C and nearest RHS N148D;

Veins: 13 to 14 pairs with midrib; slightly impressed adaxial and costate and smooth abaxial;

Vein color: Adaxial margin nearest RHS 189A, center nearest RHS 160C; adaxial margin nearest RHS 191B, and center nearest RHS 160D;

Petiole: Glabrous and matte both adaxial and abaxial; moderately concavo-convex; stiff; to 33 cm long and 17 mm wide at the base and about 8 mm deep, average about 30 cm long and 15 mm wide and 7 mm deep;

Petiole color: Adaxial and abaxial margin nearest RHS 138A, adaxial center between RHS 145B and RHS 145C, abaxial center between RHS 145D and RHS 155C;

Flower description:

Buds one to two days prior to opening: Clavate with acute apex and narrow tube and rounded base; about 37 mm long and 10 mm in diameter at the widest portion in the bulb, tube to about 15 mm long and to about 3 mm diameter at the base, gradually tapering from bulb;

Bud color: Between RHS 85D and RHS 85C in the distal bulb portion, nearest RHS 85D in the proximal bulb portion, and between RHS 85D and RHS NN155B in the outer corolla tube;

Flowers: Perfect; incomplete; campanulate; with acute apex and rounded base; attitude outwardly to slightly downwardly; to 50 mm long to exserted pistil; corolla to 44 mm long and 28 mm wide at apex, fused in basal 27 mm, free in the distal 17 mm; decreasing in size distally; corolla tube portion 15 mm long and gradually tapering to 4 mm diameter at base; decreasing in size distally; flowers tightly arranged on scape;

Flowering lasting: Persists for a normal period, usually about one day on plant;

Flowering period: Scapes remain effective with flowers beginning late June for about three weeks; with about 40 flowers per scape; mostly secund;

Fragrance: No detectable fragrance;

Tepals: Two sets of three; clavate; entire margins; acute apex; fused in basal 27 mm; glabrous adaxial and abaxial; inner set with 1 mm wide translucent margin; outer set to about 9 mm wide and 44 mm long; inner set to about 10 mm wide and 44 mm long;

Tepal color: Both sets identical; adaxial nearest RHS 85C in the longitudinal center and nearest RHS NN155D along edges, abaxial lighter than RHS 85D;

Gynoecium: Single; to about 51 mm long; superior;

*Style*.—Cylindrical; glabrous; to about 50 mm long and 0.5 mm diameter; with distal 5 mm arcuate upwards about 90 degrees; color distally nearest RHS NN155C transitioning to nearest RHS 155C in the proximally.

*Stigma*.—Puberulent; tri-lobed; about 1 mm long and 1.5 mm diameter; color nearest RHS NN155B.

*Ovary*.—Ellipsoidal; superior; apex rounded; base rounded to truncate; sides slightly furrowed, about 7 mm long and 3 mm diameter; color nearest RHS 145A.

Androecium: Six;

*Filaments*.—Six; cylindrical; approximately 47 mm long and 0.5 mm in diameter; arcuate upwardly about 90° in the distal 10 mm; color distally nearest RHS NN155C transitioning to nearest RHS 155C proximally.

*Anthers*.—Oblong with rounded ends; basifixed, longitudinally dehiscent; about 5 mm long and 2.5 mm wide when fully developed and before flower opening; color dorsal side nearest RHS 165B and ventral side nearest RHS 161C.

*Pollen*.—Abundant; spherical; less than 0.1 mm long; color nearest RHS 17A.

Peduncle: Cylindrical; usually one per mature division; about 4 per plant; glabrous; moderately glaucous; erect; to about 58 cm tall, and about 8 mm in diameter at the base, average about 54 cm tall and 7 mm diameter at base;

Inflorescence: Flowering portion about 22 cm long and 7 cm wide; with variegated bracts subtending each flower;

Peduncle color: Proximal portion below leaves between RHS 190C and RHS 148D and the distal portion between RHS N187B and RHS N187C;

Pedicel: Cylindrical; glabrous; slightly lustrous; to about 14 mm long and 2 mm diameter, decreasing in size distally; attitude outwardly to slightly arcuate outwardly;

Pedicel color: Between RHS 160D and RHS 145D;

Floral bracts: Each flower normally subtended by a single variegated bract; lanceolate; narrowly acute apex and truncate clasping base; entire margin; glabrous and slightly glaucous adaxial and abaxial, becoming lustrous in the central abaxial; to about 50 mm long 15 mm wide, decreasing distally; variegated margin about 2 to 3 mm wide;

Bract color: At flowering adaxial and abaxial margin nearest RHS NN137B, adaxial and abaxial center nearest RHS 160D, and the intermediate zone nearest RHS 146D;

Fruit: Tri-valved dehiscent capsule; oblong; apiculate apex and truncate base; lightly furrowed; about 25 mm long and 4 mm diameter; in maturity nearest RHS 164C;

Seed: Typically about 12 to 18 per capsule under natural pollination; endospermic; flattened-elliptic wing surrounding embryo situated toward one end of ellipse; up to 11 mm long and 2.5 mm wide and 1 mm thick at embryo; color nearest RHS 202A;

Disease and pest resistance: Resistance to pests (including: *Odocoileus virginianus* and *Oryctotagus cuniculus*) and diseases common to *Hostas* is equal that typical of other cultivars;

Growth: The plant grows best and shows best coloration with plenty of moisture, adequate drainage, and light shade, but is able to tolerate some drought when mature.

Hardiness: At least from USDA zone 3 through 8.

It is claimed:

1. A new and distinct *Hosta* plant named 'Moment to Treasure' as herein described and illustrated.

* * * * *